(12) United States Patent
Skead et al.

(10) Patent No.: US 7,034,028 B2
(45) Date of Patent: Apr. 25, 2006

(54) TREATMENT OF INFLAMMATORY DISORDERS

(75) Inventors: Benjamin Mark Skead, Cambridge (GB); Robin Mark Bannister, Essex (GB); Alan Rothaul, Essex (GB)

(73) Assignee: Arakis Ltd., (GB)

( * ) Notice: Subject to any disclaimer, the term of this patent is extended or adjusted under 35 U.S.C. 154(b) by 0 days.

(21) Appl. No.: 10/362,784

(22) PCT Filed: Aug. 31, 2001

(86) PCT No.: PCT/GB01/03924

§ 371 (c)(1), (2), (4) Date: Aug. 28, 2003

(87) PCT Pub. No.: WO02/19994

PCT Pub. Date: Mar. 14, 2002

(65) Prior Publication Data

US 2004/0029916 A1 Feb. 12, 2004

(30) Foreign Application Priority Data

Sep. 5, 2000 (GB) .................................. 0021776.0

(51) Int. Cl.
- A61K 31/44 (2006.01)
- A61K 31/47 (2006.01)
- A61K 31/445 (2006.01)
- A61K 31/495 (2006.01)

(52) U.S. Cl. ...................... 514/250; 514/299; 514/313; 514/314; 514/315

(58) Field of Classification Search ................ 514/313, 514/299, 314, 315, 250
See application file for complete search history.

(56) References Cited

U.S. PATENT DOCUMENTS

| | | | |
|---|---|---|---|
| 5,776,977 A * | 7/1998 | Naik et al. | ................... 514/532 |
| 6,197,788 B1 | 3/2001 | Fletcher et al. | |
| 6,572,858 B1 | 6/2003 | Charous | |

FOREIGN PATENT DOCUMENTS

| | | |
|---|---|---|
| WO | WO 90/00055 | 1/1990 |
| WO | WO 98/39003 | 9/1998 |
| WO | WO 00/66107 | 9/2000 |

OTHER PUBLICATIONS

Berqvost et al. (1983) "Distribution of chloroquine and its metabolite desethylchloroquine in human blood cells" *J. of Chromatography* 272(1):137-48, (abstract only).

Bates, Edna J. et al. "Stimulation of human neutrophil degranulation by mefloquine" *Int. Arch. Allergy Appl. Immunol.* (1988) 86(4), 446-52.

Fontagne, J. et al. "Effects of some antimalarial drugs on rat inflammatory polymorphioneuclear leukocyte function" *Biomed. Pharmacother.* (1989) 43(1) 43-51.

Goldring, J.P. Dean and Sharon Nemaorani (1999) "Antimalarial drugs modulate the expression of monocyte receptors" *International Journal of Immunopharmacology* 21:599-607.

Rainsford K D "effects of antimalarial drugs on interleukin 1-induced cartilage proteglycan degradation in-vitro" *J. Pharmacy and Parmacology* (1986) 38(11), 829-833.

* cited by examiner

Primary Examiner—Sreeni Padmanabhan
Assistant Examiner—Jennifer Kim
(74) Attorney, Agent, or Firm—Saliwanchik, Lloyd & Saliwanchik

(57) ABSTRACT

A method of treating an inflammatory disease or an autoimmune disease in a subject, comprises the administration of mefloquine.

1 Claim, No Drawings

TREATMENT OF INFLAMMATORY DISORDERS

This application is a National Stage Application of International Application Number PCT/GB01/03924, published, pursuant to PCT Article 21(2).

FIELD OF THE INVENTION

This invention relates to the treatment of inflammatory disorders.

BACKGROUND OF THE INVENTION

Cytokines belong to a large group of polypeptide- or glycopeptide-signaling molecules that act, at extremely low concentrations, as regulators of cell growth and essential mediators of inflammation and immune reactions. The production and functions of cytokines are tightly regulated by cytokines themselves and by several other factors. Most cytokines act locally and are implicated in a number of inflammatory conditions. These include rheumatoid arthritis (RA), osteoarthritis (OA), psoriatic arthritis, psoriasis, ulcerative colitis and Crohn's disease.

The antimalarial compounds chloroquine and hydroxychloroquine are known as broadly active, modestly potent inhibitors of cytokines. Such antimalarial agents have become important disease-modifying antirheumatic agents (DMARD) in the second line treatment of rheumatoid arthritis and other inflammatory disorders. Other agents in this class include gold, penicillamine, methotrexate and cyclosporins, all of which have potent activity. However, the utility of these latter drugs for the treatment of a chronic disease such as rheumatoid arthritis is limited by serious side-effects. The antimalarial agents in the DMARD class are recognised as having a more moderate side-effect profile, while possibly lacking the potency of some of the other agents. However, there is still concern about the ocular side-effects of both chloroquine and hydroxychloroquine. Thus, it may be postulated that a drug for the treatment of arthritis that possesses an improved efficacy versus side-effect profile over hydroxychloroquine, the most significant antimalarial drug in the DMARD class, would be of significant clinical potential.

In terms of antimalarial potency, mefloquine is one of the most effective drugs indicated for both prophylaxis and treatment and has particular utility for use in chloroquine-resistant malaria. Chloroquine has been the mainstay of antimalarial treatment and prophylaxis, but the emergence of chloroquine resistance in *Plasmodium falciparum*, the most lethal strain, has started to limit its utility. Thus mefloquine has emerged as the preferred compound for the prophylaxis and treatment of malignant malaria.

Mefloquine enantiomers have been evaluated in animal models for efficacy against *Plasmodium* species. These studies concluded that there was no difference in antimalarial potency of the enantiomers.

SUMMARY OF THE INVENTION

Surprisingly, it has been found that (+)-mefloquine possesses potent anti-rheumatic properties. The use of the substantially pure enantiomer may maximise efficacy and reduce unwanted side-effects. (+)-Erythro-mefloquine is a more potent inhibitor of cytokines implicated in the inflammatory response. (+)-Erythro-mefloquine suppresses human lymphocyte proliferation.

DESCRIPTION OF THE INVENTION

The present invention is based, at least in part, on the finding that mefloquine shows a broad profile of cytokine inhibition, consistent with antimalarial RA therapy. In addition, it has been shown that the isomers of mefloquine show good activity against Interleukin-8 (IL-8). Both chloroquine and hydroxychloroquine are inactive against IL-8, and this cytokine is implicated in the progression of inflammation and tissue destruction inherent in the progress of RA and OA. This is a significant aspect of the enhanced profile of mefloquine isomers in the treatment of inflammatory conditions. In addition, as shown in Table 1, the isomers of mefloquine have superior activity over chloroquine and hydroxychloroquine against IL-2, a cytokine implicated in the destruction of connective tissue in RA and OA.

TABLE 1

Inhibition Profile ($IC_{50}$, μM)

| | TNF | IL-1 | IL-6 | IL-8 | IL-2 | T-cell proliferation | IFN gamma |
|---|---|---|---|---|---|---|---|
| Hydroxychloroquine | 32.2 | 21 | 90 | Inactive | 94 | 16 | 94 |
| Chloroquine | 21 | 6.3 | 81 | Inactive | 66 | 13 | 63 |
| (−)Mefloquine | 18 | 79 | 43 | 63 | 17 | 10 | 18 |
| (+)Mefloquine | 24 | 68 | 53 | 41 | 17 | 11 | 17 |

This inhibition profile has shown significant activity in a preclinical, ex vivo assay of tissue destruction in the bovine nasal cartilage model. The results are shown in Table 2.

TABLE 2

Inhibition of IL-2-stimulated bovine nasal cartilage destruction

| | 1 μM | 10 μM | 100 μM |
|---|---|---|---|
| Hydroxychloroquine | 4 | 3 | 36 |
| Chloroquine | 3 | 6 | 35 |
| (+/−) Mefloquine | | 20 | |
| (−) Mefloquine | 37 | 45 | 82 |
| (+) Mefloquine | 32 | 44 | 71 |

For use in the invention, the active agent may be formulated, e.g. together with a carrier, excipient or diluent, and administered, by procedures that are known in the art, including those already proposed for the racemate. Suitable compositions will depend on the intended route of administration, which may be, for example, oral, topical, nasal, rectal, sublingual, buccal or transdermal. Sustained, delayed, timed or immediate release compositions may be used.

The amount of the agent that should be administered can readily be determined by the skilled man, taking into account the usual factors such as the type of patient, the nature of the condition being treated, and the route of administration. The amount of enantiomer may be higher or the same as that for the racemate, or may be modified depending on the co-administration of other drugs.

Conditions that may be treated include conditions involving cartilage destruction, inflammatory conditions and those mediated by L-2 and IL-6, e.g. rheumatoid arthritis, asthma, psoriasis, psoriatic arthritis, Crohn's disease, irritable bowel syndrome and systemic lupus erythematosus. Other relevant conditions are ulcerative colitis, COPD and asthma. The patient may be disposed to CNS side-effects, and/or may be undergoing concomitant therapy with another drug.

Depending on the relative activities of the individual enantiomers, it may be preferred to administer a mixture, e.g. racemate, or substantially one enantiomer. The desired enantiomer may be in at least 50%, 70%, 90%, 95% or 99% excess, with respect to any other. The active agent may be used in any active form, e.g. salt or non-salt.

The use of (+)-erythro-mefloquine is preferred. It appears that this compound is particularly useful in providing the desired effect, without tissue destruction, and can be safely administered at a relatively high dosage.

The invention claimed is:

1. A method for inhibiting IL-2 and/or IL-8 production in a patient in need thereof, wherein said method comprises administering an effective amount of (+)-erythro-mefloquine to said patient, wherein said patient is diagnosed with rheumatoid arthritis or osteoarthritis.

* * * * *